US012121506B1

(12) United States Patent
Smith et al.

(10) Patent No.: US 12,121,506 B1
(45) Date of Patent: Oct. 22, 2024

(54) ARTESUNATE POWDERS, PHARMACEUTICAL COMPOSITIONS AND METHODS OF MANUFACTURE

(71) Applicant: AMIVAS, INC., Wilmington, DE (US)

(72) Inventors: Bryan L. Smith, Chevy Chase, MD (US); Lisa Thomas Read, Boonsboro, MD (US)

(73) Assignee: AMIVAS, INC., Wilmington, DE (US)

( * ) Notice: Subject to any disclaimer, the term of this patent is extended or adjusted under 35 U.S.C. 154(b) by 0 days.

(21) Appl. No.: 18/443,850

(22) Filed: Feb. 16, 2024

(51) Int. Cl.
  *A61K 31/357* (2006.01)
  *A61K 9/00* (2006.01)
  *A61K 9/14* (2006.01)
  *B65B 1/04* (2006.01)
  *B65B 55/12* (2006.01)

(52) U.S. Cl.
  CPC .......... *A61K 31/357* (2013.01); *A61K 9/0019* (2013.01); *A61K 9/14* (2013.01); *B65B 1/04* (2013.01); *B65B 55/12* (2013.01)

(58) Field of Classification Search
  None
  See application file for complete search history.

(56) References Cited

U.S. PATENT DOCUMENTS

| 7,678,828 | B2 | 3/2010 | Ellis et al. |
| 2009/0192216 | A1* | 7/2009 | Ellis ................ A61K 31/357 |
| | | | 514/450 |

| 2017/0326102 | A1* | 11/2017 | Raut ................ A61K 31/4709 |
| 2019/0029996 | A1* | 1/2019 | Zhao ................ A61P 33/12 |
| 2023/0263768 | A1* | 8/2023 | Le ................ A61K 9/1652 |
| | | | 514/450 |

FOREIGN PATENT DOCUMENTS

| CN | 107582529 A | * | 1/2018 | |
| CN | 109172519 A | * | 1/2019 | |
| CN | 109734983 A | * | 5/2019 | |
| WO | WO-2021258206 A1 | * | 12/2021 | ............. A61K 31/15 |

OTHER PUBLICATIONS

Kalman. "Effect of moisture content on flowability: Angle of repose, tilting angle, and Hausner ratio." Powder Technology, vol. 393, 2021, pp. 582-596. (Year: 2021).*
National Weather Service, La Crosse, Wisconsin Weather Forecast Office. "Dew Point vs. Humidity." https://www.weather.gov/arx/why_dewpoint_vs_humidity accessed May 21, 2024, 1 page. (Year: 2024).*
English Translation of CN 109734983 A. Obtained by examiner on May 20, 2024, originally published in Chinese on May 10, 2019, 6 printed pages. (Year: 2019).*

(Continued)

*Primary Examiner* — Isaac Shomer
(74) *Attorney, Agent, or Firm* — BUCHANAN INGERSOLL & ROONEY PC

(57) ABSTRACT

Disclosed herein are powders including a therapeutically effective amount of 4-oxo-4-[[(1R,4S,5R,8S,9R,10S,12R,13R)-1,5,9-trimethyl-11,14,15,16-tetraoxatetracyclo [10.3.1.0$^{4,13}$.0$^{8,13}$]1exadecane-10-yl]oxy]butanoic acid (artesunate) or a pharmaceutically acceptable salt thereof that can be easily manufactured, sterilized and packaged. Processes for producing these powders and pharmaceutical compositions containing these powders are also disclosed.

18 Claims, 8 Drawing Sheets

(56) References Cited

OTHER PUBLICATIONS

Google Patents. English Translation of CN 109172519 A. Obtained from https://patents.google.com/patent/CN109172519A/en?oq=CN+109172519 on May 20, 2024, originally published in Chinese on Jan. 11, 2019, pp. 1-4. (Year: 2019).*

English Translation of CN 107582529 A. Obtained by examiner on May 20, 2024, originally published in Chinese on Jan. 16, 2018, 7 printed pages. (Year: 2018).*

Haynes, R. et al. "C-10 Ester and Ether Derivatives of Dihydroartemisinin-10α Artesunate, Preparation of Authentic 10-62 Artesunate, and of Other Ester and Ether Derivatives Bearing Potential Aromatic Intercalating Groups at C-10" Eur. J. Org. Chem. (2002) pp. 113-132.

"Artesunate for Injection, for Intravenous use Initial U.S. Approval: 2020", Package Insert for Amivas LLC, Revised: May 2020, (14 pages).

Agnihotri et al., "Formal Chemical Stability Analysis and Solubility Analysis of Artesunate and Hydroxychloroquinine for Development of Parenteral Dosage Form", Journal of Pharmacy Research, Jan. 2013, vol. 6, pp. 117-122.

* cited by examiner

ARTESUNATE POWDERS, PHARMACEUTICAL COMPOSITIONS AND METHODS OF MANUFACTURE

FIELD

The present disclosure relates to powders and pharmaceutical compositions comprising 4-oxo-4-[[(1R,4S,5R,8S,9R,10S,12R,13R)-1,5,9-trimethyl-11,14,15,16-tetraoxatetracyclo[10.3.1.0$^{4,13}$.0$^{8,13}$]hexadecan-10-yl]oxy]butanoic acid (artesunate) or a pharmaceutically acceptable salt thereof. Processes for preparing the powders and compositions are also disclosed.

BACKGROUND INFORMATION

Artesunate has historically been derived as a derivative of artemisinin, the active antimalarial component isolated from herb *Artemisia annua* in 1972, and synthesized by reacting dihydroartemisinin with succinic acid anhydride in basic medium. Artesunate has since been widely studied, and has been effective in broader treatments for cancer, as an antiviral, treatment of inflammatory and immune diseases, and in other parasitic infections.

Artesunate has been used to treat severe malaria in the United States and elsewhere. For example, Artesunate for Injection™, supplied by Amivas Inc., is an antimalarial indicated for the initial treatment of severe malaria in adult and pediatric patients. Artesunate for Injection™ is administered intravenously as a slow bolus over 1 minute to 2 minutes. The recommended dosage of Artesunate for Injection™ is 2.4 mg/kg at 0 hours, 12 hours, 24 hours, and thereafter administered once daily until the patient is able to tolerate oral antimalarial therapy. Artesunate for Injection™ is supplied as a 110 mg, white or almost white, sterile, fine crystalline powder for constitution in single-dose, clear glass vials sealed with a rubber stopper (not made with natural rubber latex) and an aluminum overseal.

Artesunate is soluble in organic solvents, such as acetone and methanol, and is slightly soluble in water. It can be administered orally, rectally via suppositories, or via intramuscular or intravenous injection. Many studies have found that artesunate is unstable under basic and acidic conditions. It is also susceptible to degradation by moisture and heat (Agnihotri J. et al, J Pharmacy Res, 2013, 6:117-122). Therefore, historically, artesunate injection has to be prepared immediately prior to use.

Artesunate is typically distributed in powder form, sterilized and packaged in vials or other appropriate packaging for distribution. The accurate dispersion of artesunate powder into packaging materials has proven to be challenging due to the clumping of powder material during the filling of the capsules, vials, or other packaging materials. Indeed, powder clumping can lead to the formation of sticky masses, or "fish eyes" (powder lumps with a hydrated skin and dry core), which can disrupt commercial manufacturing processes by clogging filling/dosing machines and producing products with inaccurate concentrations of the artesunate powder.

Thus, to address the foregoing issues, a sterilized artesunate powder product which can be easily manufactured, sterilized and packaged is disclosed herein. The powders disclosed herein can be used for accurate, consistent, and easy dosing into packaging materials.

SUMMARY

Disclosed herein is a powder including (i.e., comprising) a therapeutically effective amount of 4-oxo-4-[[(1R,4S,5R,8S,9R,10S,12R,13R)-1,5,9-trimethyl-11,14,15,16-tetraoxatetracyclo[10.3.1.0$^{4,13}$.0$^{8,13}$]hexadecan-10-yl]oxy]butanoic acid (artesunate) or a pharmaceutically acceptable salt thereof that can be easily manufactured, sterilized and packaged.

Also disclosed herein is a process for the preparation of the powders disclosed herein, the process including at least one or more of: micronizing a raw artesunate ingredient into an artesunate powder; and sterilizing the artesunate powder with ethylene oxide.

Disclosed herein is a pharmaceutical composition including any of the powders disclosed herein and a buffer solution, wherein the pharmaceutical composition is formulated for intravenous injection.

BRIEF DESCRIPTION OF THE DRAWING(S)

Other features and advantages of the powders, processes and compositions disclosed herein will be apparent to those skilled in the art reading the following detailed description in conjugation with the exemplary embodiments illustrated in the drawings, wherein.

Figure 6:
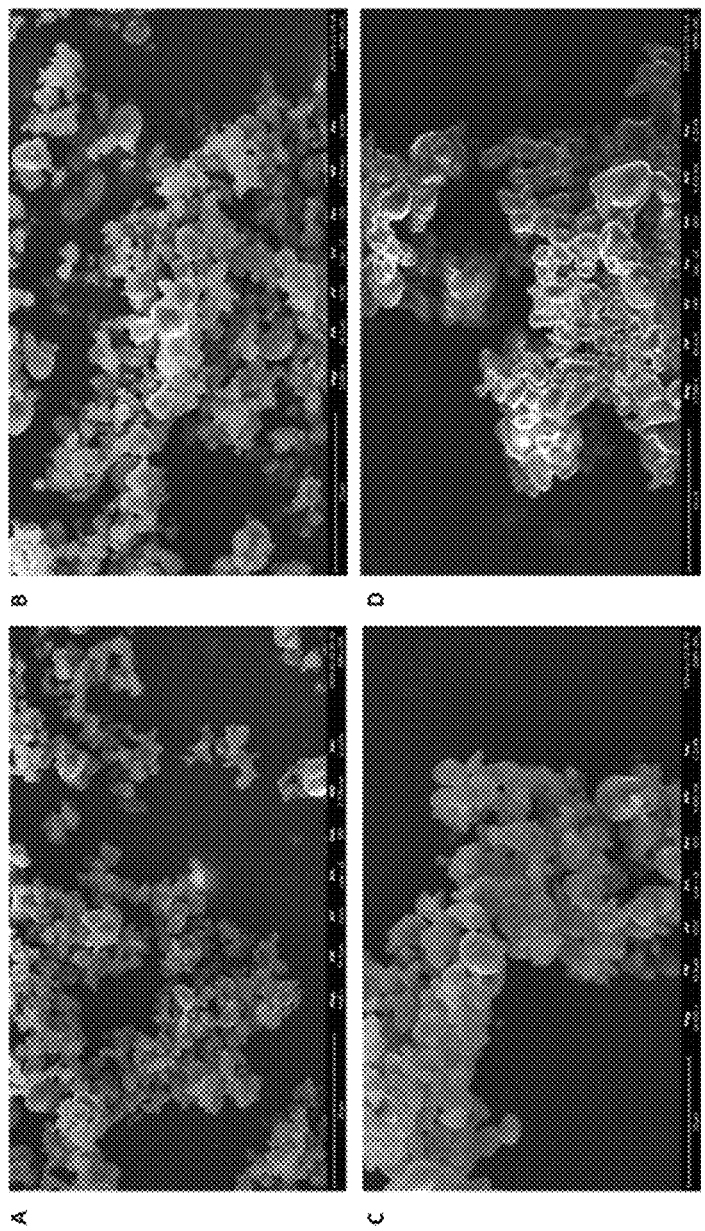

FIG. 6 depicts scanning electron microscope (SEM) photographs of an artesunate powder at 35% relative humidity. Part A of FIG. 6 is a SEM photograph of the artesunate powder taken at a magnification of 9400×. Part B of FIG. 6 is a SEM photograph of the artesunate powder taken at a magnification of 13000×. Part C of FIG. 6 is a SEM photograph of the artesunate powder taken at a magnification of 16000×. Part D of FIG. 6 is a SEM photograph of the artesunate powder taken at a magnification of 17500×.

Figure 7:
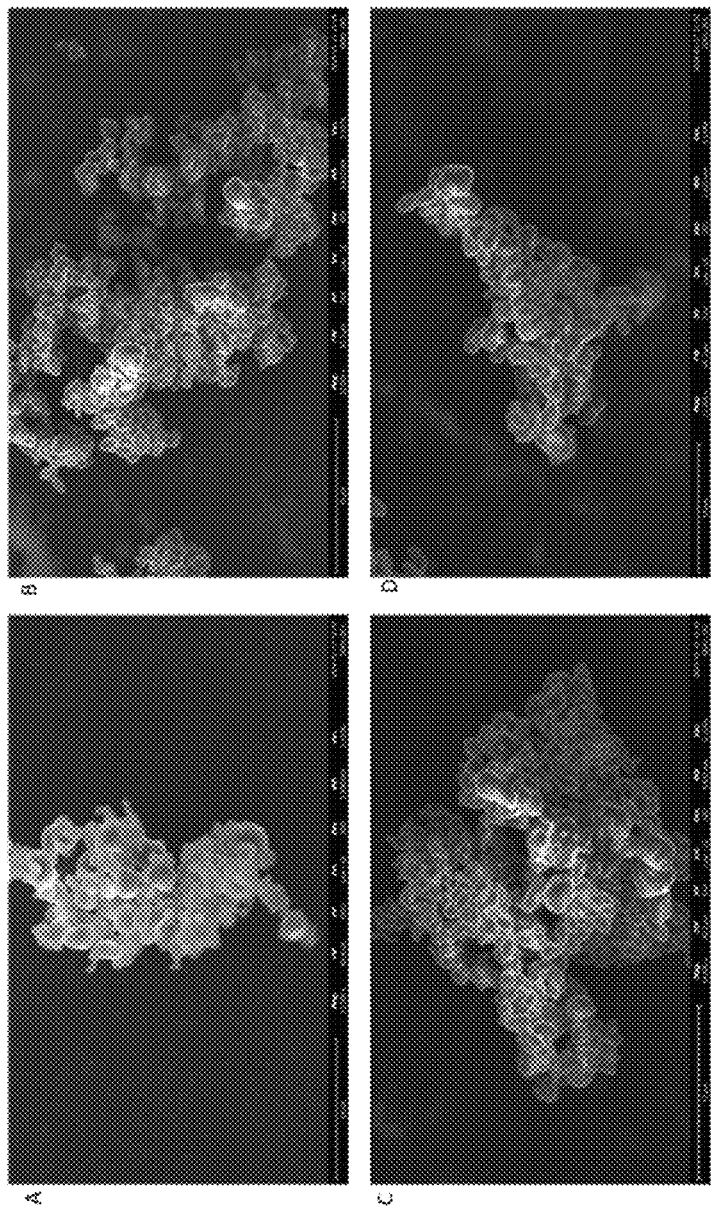

FIG. 7 depicts scanning electron microscope (SEM) photographs of an artesunate powder at 20% relative humidity. Part A of FIG. 7 is a SEM photograph of the artesunate powder taken at a magnification of 11500×. Part B of FIG. 7 is a SEM photograph of the artesunate powder taken at a magnification of 12500×. Part C of FIG. 7 is a SEM photograph of the artesunate powder taken at a magnification of 14000×. Part D of FIG. 7 is a SEM photograph of the artesunate powder taken at a magnification of 15500×.

Figure 8:
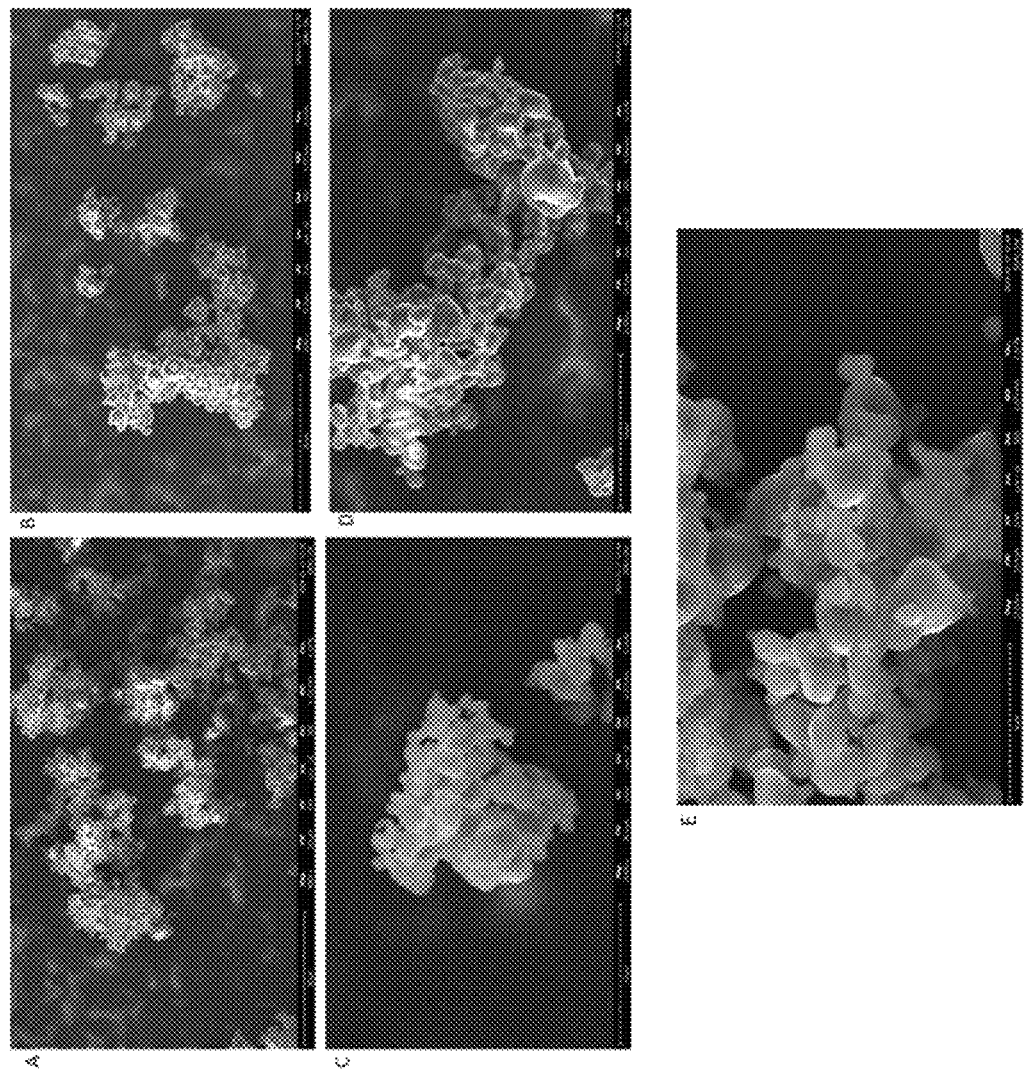

FIG. 8 depicts scanning electron microscope (SEM) photographs of an artesunate powder at 50% relative humidity. Part A of FIG. 8 is a SEM photograph of the artesunate powder taken at a magnification of 6000×. Part B of FIG. 8 is a SEM photograph of the artesunate powder taken at a magnification of 9200×. Part C of FIG. 8 is a SEM photograph of the artesunate powder taken at a magnification of 19000×. Part D of FIG. 8 is a SEM photograph of the artesunate powder taken at a magnification of 21500×. Part E of FIG. 8 is a SEM photograph of the artesunate powder taken at a magnification of 23500×.

DESCRIPTION OF THE INVENTION

One aspect of the present disclosure is a powder including a therapeutically effective amount of 4-oxo-4-[[(1R,4S,5R, 8S,9R,10S,12R,13R)-1,5,9-trimethyl-11,14,15,16-tetraoxa-tetracyclo[10.3.1.0$^{4,13}$.0$^{8,13}$]hexadecan-10-yl]oxy]butanoic acid (artesunate) or a pharmaceutically acceptable salt thereof that can be easily manufactured, sterilized and packaged.

In exemplary embodiments, the powder has an average static charge from −0.05 kV to 0.05 kV, according to a static charge test that includes (i) subjecting the powder to a relative humidity of 30% to 40% for at least five days, (ii) placing the powder onto a piece of weigh paper, (iii) measuring the static charge of the powder with a static meter at least three times, wherein the measuring of the static charge of the powder with a static meter occurs at least 25 millimeters from the surface of the powder and (iv) calculating the average static charge from the measured static charges. In exemplary embodiments, the powder has an average static charge from −0.1 kV to 0.1 kV according to a static charge test that includes (i) subjecting the powder to a relative humidity of 30% to 40% for at least five days, (ii) placing the powder onto a piece of weigh paper, (iii) measuring the static charge of the powder with a static meter at least three times, wherein the measuring of the static charge of the powder with a static meter occurs at least 25 millimeters from the surface of the powder and (iv) calculating the average static charge from the measured static charges.

The inventors have surprisingly discovered that relative humidity has an impact on the static charge of the artesunate powders disclosed herein. Therefore, without being bound to any particular theory, subjecting the powders disclosed herein to a relative humidity ranging from 30% to 40% is believed to render the powders disclosed herein with a neutral or near-neutral static charge. This near-neutral or neutral static charge is believed to improve the flowability and filling of the powders since the occurrence of static cling of the powders to a dosing head is either significantly reduced or absent.

In exemplary embodiments, the powder absorbs moisture in an amount from 0.01 wt % to 0.03 wt %, based on the total weight of the powder, when subjected to a relative humidity from 30% to 40%. In exemplary embodiments, the powder absorbs moisture in any amount ranging from 0.01 wt % to 0.08 wt %, based on the total weight of the powder, when subjected to a relative humidity from 30% to 40%.

The moisture absorption of the powders disclosed herein can be determined by Dynamic Vapor Sorption (DVS). DVS is a gravimetric technique that measures how quickly and how much of a solvent (e.g., water vapor) is absorbed by a sample, such as a dry powder. DVS does this by varying the vapor concentration surrounding the sample and measuring the change in mass which this produces. In exemplary embodiments, the moisture absorbance of the powders disclosed herein is measured by a DVS method that includes varying the relative humidity of the powder's environment.

In exemplary embodiments, the powder has an angle of repose of less than 40° when passing through a funnel with an opening of 8 mm to 12 mm at a relative humidity from 30% to 40%.

As used herein, an "angle of repose" is an angle between a slope of a pile of powder and a horizontal plane. The angle of repose is an indicator of the flowability of a powder and correlates with the strength of particle-particle interactions occurring in the powder.

In exemplary embodiments, the powder has an angle of repose of less than 40° when passing through a funnel having a diameter of at least 30 mm at a relative humidity from 30% to 40%.

In exemplary embodiments, the powder is micronized to a particle size having a D90 of less than 20 µm; and/or a D100 of less than 100 µm. In exemplary embodiments, the powder is micronized to a particle size having a D50 of less than 5 µm. In exemplary embodiments, the powder is micronized to a particle size having a D50 of about 4 µm.

As used herein, the terms "D50", "D90" and "D100" are known in the art to describe the mean or average size of a particle. The numbering following the letter indicates the percentage of particles that are larger or smaller than the identified size. For example, a D50 of 2 µm means the average particle size of that material is 2 µm, and that 50% of particles are smaller than 2 µm while 50% of particles are larger, or means a cumulative 50% point of diameter or pass particle size. Subsequently, a D90 identifier means that 90% of particles are smaller than the size enumerated, while 10% are larger, or a cumulative 90% pass particle size.

As used herein, the term "about" refers to a value that is ±1% of the stated value. In addition, it is understood that reference to a range of a first value to a second value includes the range of the stated values, e.g., a range of about 1 to about 5 also includes the more precise range of 1 to 5. It is also understood that the ranges disclosed herein include any selected subrange within the stated range, e.g., a subrange of about 50 to about 60 is contemplated in a disclosed range of about 1 to about 100.

The artesunate or pharmaceutically acceptable salt thereof can be prepared from either a naturally derived artemisinin, semi-synthetically derived, or completely synthetically derived. In exemplary embodiments, the artesunate or pharmaceutically acceptable salt thereof is prepared from a derivative of artemisinin (e.g., dihydroartemisinin).

As used herein, a "naturally derived artemisinin" is an artemisinin that has been synthesized by and isolated from a natural product (e.g., the leaves of *Artemisia annua*).

Naturally derived artemisinin can appear as a white powder and can include small amounts of impurities, e.g., less than 0.05% Artemisinin, less than 0.05% Dihydroartemisinin, less than 0.05% di-dehydrodeoxyartemisinin (Glycal), and less than 0.13% of other impurities (e.g., deoxyartesunic acid, 2-deoxyartesunate, succinic acid, succinic anhydride, β-artesunate, process solvents, and/or 10α, 10β-succinate dimer). As used herein, "process solvents" are solvents used to aid in the isolation and purification of artemisinin from natural products (e.g., ethyl acetate, n-heptane, methanol and/or water). Naturally derived artemisinin can have particle sizes, tested by particle size distribution (PSD), possessing a D50 of about 13.48 µm and a D90 of about 24.63 µm.

In exemplary embodiments, the artesunate or pharmaceutically acceptable salt thereof is not formed from a naturally derived artemisinin. An exemplary advantage of these embodiments is that they avoid potential sterility problems observed with artesunates or pharmaceutically acceptable salts thereof derived from naturally derived artemisinin. Indeed, the inventors have surprisingly discovered that artesunate products derived from naturally derived artemisinin can possess *Corynebacterium auris* growth, which could cause potential safety and efficacy issues.

In exemplary embodiments, the powder includes a water content of no more than 0.5%, no more than 0.5% dihydroartemisinin, no more than 0.2% didehydrodeoxyartemisinin, and/or no more than 0.2% of other impurities (e.g., deoxyartesunic acid, 2-deoxyartesunate, succinic acid, succinic anhydride, β-artesunate, process solvents, and/or 10α,10β-succinate dimer).

In exemplary embodiments, the artesunate used in the powders disclosed herein is free of *Corynebacterium auris* growth and/or prepared from a raw artesunate ingredient free of *Corynebacterium auris* growth.

In exemplary embodiments, the powder has a Hausner ratio of at least 1.6 when subjected to a relative humidity from 30% to 40%. In exemplary embodiments, the powder has a Hausner ratio ranging from 1.26 to 1.34, 1.35-1.45, or 1.46-1.59 when subjected to a relative humidity from 30% to 40%.

As used herein, a "Hausner ratio" is the ratio of a powder's tapped density to its bulk density. A Hausner ratio can be used to determine the flowability of a powder. The lower the Hausner ratio of a powder, the better the flowability. As used herein, the "bulk density" of a powder is the ratio of its mass in an untapped powder sample to its volume that includes the contribution of the interparticulate void volume of the untapped powder sample. As used herein, an "untapped powder sample" is a sample that has not been subjected to mechanical tapping in a container (e.g., a vial or measuring cylinder) before density is measured. As used herein, the "tapped density" of a powder is the density of the powder after the powder has been placed in a container and subjected to mechanically tapping.

The bulk density of the powders disclosed herein can be determined with the use of a graduated cylinder, a volumeter or a vessel.

In exemplary embodiments, the bulk density of the powder is determined with a graduated cylinder by a procedure including: (i) passing a quantity of powder through a sieve with apertures greater than or equal to 1.0 mm, if necessary, to break up agglomerates that may have formed during storage, manufacturing and/or handling; (ii) transferring the sieved powder into a dry graduated cylinder (e.g., a 250 mL graduated cylinder); (iii) gently introducing, without compacting, approximately 100 g of the powder weighed (m) with 0.1% accuracy; (iv) carefully leveling the powder without compacting, if necessary; (v) reading the unsettled apparent volume ($V_0$) to the nearest graduated unit; and (vi) calculating the bulk density in g per mL by the formula $m/V_0$. This procedure can be replicated to produce a more accurate measurement of the powder's bulk density. If the powder density is too low or too high, such that the test sample has an untapped apparent volume of either more than 250 mL or less than 150 mL, it is not possible to use 100 g of powder sample. Therefore, a different amount of powder has to be selected as test sample, such that its untapped apparent volume is between 150 mL to 250 mL (apparent volume greater than or equal to 60 percent of the total volume of the cylinder). For test samples having an apparent volume between 50 mL and 100 mL, a 100 mL cylinder readable to 1 mL can be used. This procedure can be replicated to produce a more accurate measurement of the powder's bulk density.

In exemplary embodiments, the bulk density of the powder is determined with a volumeter by a procedure including: (i) allowing a minimum of 25 $cm^3$ of powder to flow through the volumeter into a sample receiving cup until the cup overflows; (ii) carefully scraping excess powder from the top of the cup by smoothly moving the edge of a blade of a spatula perpendicular to and in contact with the top surface of the cup, taking care to keep the spatula perpendicular to prevent packing or removal of powder from the cup; (iii) removing any material from the side of the cup; (iv) determining the mass (m) of the powder to the nearest 0.1% in the cup; and (v) calculating the bulk density in g per mL by the formula $m/V_0$, in which $V_0$ is the volume of the cup. This procedure can be replicated to produce a more accurate measurement of the powder's bulk density.

In exemplary embodiments, the volumeter includes at least one or more of a top funnel fitted with a 1.0 mm sieve, a baffle box and/or a cup. The funnel can be mounted over the baffle box, which can optionally contain four glass baffle plates. The baffle box can be located at the bottom of the volumeter and act as a funnel that collects the powder and pours into the cup mounted directly below it. The cup can be cylindrical (e.g., 25.00±0.05 mL volume with an inside diameter of 30.00±2.00 mm) or cubical (e.g., 16.39±0.20 mL volume with inside dimensions of 25.4±0.076 mm).

In exemplary embodiments, the bulk density of the powder is determined with a vessel by a procedure including: (i) passing a quantity of powder through a 1.0 mm sieve, if necessary, to break up agglomerates that may have formed during manufacturing, storage and handling of the powder; (ii) allowing the obtained powder sample to flow freely into a measuring vessel until it overflows; (iii) carefully scraping the excess powder from the top of the vessel; (iv) determining the mass (m0) of the powder to the nearest 0.1% by subtracting the mass of the filled vessel by the mass of the empty vessel; and (iv) calculating the bulk density (g/mL) by the formula m0/100. This procedure can be replicated to produce a more accurate measurement of the powder's bulk density.

In exemplary embodiments, the vessel is a 100 mL cylindrical vessel of stainless steel having a width ranging from 50 to 60 mm and a height ranging from 50 to 55 mm.

The tapped density of the powders disclosed herein can be determined with the use of a graduated cylinder, a settling apparatus and/or a vessel.

In exemplary embodiments, the tapped density of the powder is determined with a graduated cylinder and a settling apparatus by a procedure including: (i) determining the bulk volume ($V_0$) of the powder in the sample; (ii) securing the graduate cylinder in the settling apparatus; (iii) tapping the graduate cylinder 10, 500 and 1250 times and determining the corresponding volumes V10, V500 and V1250 to the nearest graduated unit; (iv) calculating the tapped density (g/mL) using the formula $m/V_f$, in which $V_f$ is the final tapped volume. If the difference between V500 and V1250 is less than or equal to 2 mL, V1250 is the tapped volume. If the difference between V500 and V1250 exceeds 2 mL, repeat in increments such as 1250 taps, until the difference between succeeding measurements is less than or equal to 2 mL. This procedure can be replicated to produce a more accurate measurement of the powder's tapped density.

In exemplary embodiments, the settling apparatus is capable of producing, in 1 min, either nominally 250±15 taps from a height of 3±0.2 mm, or nominally 300±15 taps from a height of 14±2 mm. The settling apparatus can also include a support for a graduated cylinder, e.g., a holder.

In exemplary embodiments, the powder has a bulk density below 0.2 g/mL when subjected to a relative humidity from 30% to 40%.

In exemplary embodiments, the powder has a tap density above 0.3 g/mL when subjected to a relative humidity from 30% to 40%.

In exemplary embodiments, the powder includes a crystalline form of artesunate or the pharmaceutically acceptable salt thereof in a concentration above 0 wt % to about 1 wt % of the total weight of the powder. The crystalline form of artesunate or of the pharmaceutically acceptable salt thereof can be the 10-α artesunate crystalline form and/or the 10-β artesunate crystalline form. The 10-α artesunate crystalline form and the 10-β artesunate crystalline form of artesunate can be found in the Cambridge Crystallographic Data Centre (CCDC) (see the FAHFAV, den2, and artesu crystal structures). In exemplary embodiments, the powder includes only the crystalline, or synthetic, form of artesunate or the pharmaceutically acceptable salt thereof.

In exemplary embodiments, the powder comprises semi-synthetic artesunate wherein the powder is partially synthetically derived and partially vegetal derived. As used herein, the term "vegetal" means derived from the natural plant *Artemisia annua* or another similar herb.

In exemplary embodiments, the powder includes a crystalline form of artesunate, or a pharmaceutically acceptable salt thereof, that has a XRPD pattern containing at least one or more of the following peaks: 9.41°±0.2, 9.62°±0.2, 12.29°±0.2, 12.62°±0.2, 13.0°±0.2, 15.5°±0.2, 16.77°±0.2, 18.60°±0.2, 19.68°±0.2, 19.88°±0.2, 20.34°±0.2, 20.94°±0.2, 22.0°±0.2, 22.59°±0.2, 22.95°±0.2 and/or 34.48°±0.2 2θ.

Another aspect of the present disclosure is a process for the preparation of the powders disclosed herein, the process including at least one or more of: micronizing a raw artesunate ingredient into an artesunate powder; and sterilizing the artesunate powder with ethylene oxide.

As used herein, a "raw artesunate ingredient" is an artesunate compound or ingredient that has not yet been processed into a powder. In exemplary embodiments, the raw artesunate ingredient is not formed from a naturally derived artemisinin. In exemplary embodiments, the "raw artesunate ingredient" does not possess an excipient. As used herein, an "excipient" is any compound or ingredient that can be added to the raw artesunate ingredient that does not have pharmacological properties in the quantity used and provides some other beneficial property to the raw artesunate ingredient, such as improved processing, solubility or dissolution, drug delivery or stability.

As used herein, "micronizing" or "micronization" is a process of reducing the average diameter of a material's particles. Micronizing is traditionally accomplished by mechanical means, such as milling and grinding. The crystals of artesunate powders are plates in their natural state but form into rounded spheres after micronization. The formation of rounded spheres can lower the occurrence of sticking, thereby providing a better flow of the powder.

In exemplary embodiments, the powders as disclosed herein are packaged in at least three polyethylene fiber containers prior to sterilizing of the powders. As used herein, a "polyethylene fiber container" is any container comprised of polyethylene fibers, or any regular or high-density polyethylene plastic container. In exemplary embodiments, the polyethylene fiber containers are bags or pouches made of polyethylene fibers. In exemplary embodiments, the powders are sterilized with ethylene oxide sterilization, which can penetrate breathable packaging, such as polyethylene fiber containers, to deliver a required sterility assurance level. In exemplary embodiments, the powders disclosed herein are packaged in at least one or more (e.g., at least three) Tyvek® bags (TYVEK® is a DuPont trademark for flashspun nonwoven HDPE fiber) and/or autoclavable high density polyethylene bags.

The powders disclosed herein can undergo bulk powder sterilization either before or after they are packaged into a container. The gas ethylene oxide can be used for bulk sterilization. Bulk sterilization processes can involve first treating the powders disclosed herein with ethylene oxide gas in a gas chamber for one hour at 102° F. and at 100% humidity, and, after one hour, evacuating the ethylene oxide gas from the gas chamber. Bulk sterilization processes can also involve evacuating the ethylene oxide gas from the gas chamber and then flushing the powders in the gas chamber with nitrogen gas at least twice and/or air at least once at a constant temperature of 102° F.

In exemplary embodiments, the sterilized powders as described herein are filled into a container under aseptic conditions and at a relative humidity from 30% to 40%. As used herein, the container is any vessel capable of storing the powder and may include polyethylene fiber containers, glass or plastic syringes, glass ampoules, or glass vials. As used herein, the glass vials are depyrogenated borosilicate clear glass vials, e.g., Type 1 glass vials.

In exemplary embodiments, the filling of the sterilized powders is conducted at a temperature from 15° C. to 30° C.

In exemplary embodiments, the filling of the sterilized powders is performed with a dosing system equipped with a dosing head. In exemplary embodiments, the dosing head has an opening of at least 2.5 mm. The "dosing system" can be, but is not required to be, a dosing machine which provides a semi-automatic process for powder dosing. One example of a semi-automatic dosing system is the Quantos Dosing System. It is to be understood that a variety of dosing systems known to those of ordinary skill in the art can be used in the filling of the sterilized powders disclosed herein, including dosing systems not specifically disclosed herein. The physical powder dosing can be fully automated, reproducible, and provide a 100% weight check. The autosampler can allow for up to 30 samples to be dispensed in one unattended run. As used herein, the "dosing head" is the mechanical component which dispenses the powder. The dosing heads are designed to handle a range of different powder characteristics. Generally, 12 dosing heads are offered for various applications depending on the powder's flowability, particle size and target dose weight.

In exemplary embodiments, the sterilized powder is pre-mixed in the dosing head of the dosing system before being filled into a container of choice.

In exemplary embodiments, the container is the depyrogenated borosilicate clear glass vial as previously described.

In exemplary embodiments, the process for preparing the powders disclosed herein includes filling the sterilized powders into a container under a controlled relative humidity system.

The controlled relative humidity system can include a humidifier and/or a dehumidifier programmed to control and maintain a set relative humidity.

In exemplary embodiments, the process for preparing the powders disclosed herein includes measuring the relative humidity of the environment before filling the sterilized powders into a container; and, when the humidity is outside the range of 30 to 40%, adjusting the humidity of the environment to a humidity within the range of 30 to 40%, with a controlled relative humidity system, before filling the sterilized powders into the container.

Another aspect of the present disclosure is a pharmaceutical composition comprising the powders as described herein and a buffer solution. In exemplary embodiments, the pharmaceutical composition is formulated for intravenous injection.

In exemplary embodiments, the buffer solution is a bicarbonate buffer solution that acts as a dissolution medium. In exemplary embodiments, the buffer solution includes sodium phosphate monobasic monohydrate, sodium phosphate dibasic dihydrate, sodium hydroxide, phosphoric acid, and water.

In exemplary embodiments, the buffer solution contains phosphate ions in a concentration of 0.30±0.05 M. In exemplary embodiments, the buffer solution has a pH of 8.0±0.03. Slight variations from these values are acceptable. The buffer solutions disclosed herein can be manufactured by mixing appropriate weights of monobasic and dibasic sodium phosphate compounds in distilled water until a desired molarity of phosphate ions and pH values are reached. To maintain sterility, the buffer solution can be sterilized by filtration through a filter into vials. In exemplary embodiments, the filter contains at least one or more pores with a size of 0.22μ. Alternatively, the buffer solution can be sterilized by terminal sterilization via known methods in the art, including but not limited to, ethylene oxide, radiation, moist heat (steam), dry heat, hydrogen peroxide, ozone, chlorine dioxide, supercritical carbon dioxide, and nitrogen dioxide.

The pharmaceutical compositions disclosed herein can be administered to patients in a therapeutically effective amount via intravenous injection, intramuscular injection and/or rectal administration. As used herein, the term "therapeutically effective amount" refers to any amount that is required to bring about a desired beneficial effect. For example, a therapeutically effective amount is any amount that can either slow progression of a disease (e.g., malaria) in a patient, ameliorate the symptoms of a disease in a patient, and/or reverse the progression of a disease in a patient. The desired beneficial effect arising from the use of therapeutically effective amounts of the powders disclosed herein can vary depending on the disease being treated.

As used herein, "intravenous injection" can be achieved via parenteral administration, e.g., intravenous administration. In exemplary embodiments, the pharmaceutical compositions disclosed herein are intravenously administered to a patient in an amount ranging from 1-8 mg/kg of body weight. In exemplary embodiments, the pharmaceutical compositions disclosed herein are parenterally administered to a patient in an amount of 10 mg/mL. In exemplary embodiments, the pharmaceutical compositions disclosed herein are intravenously administered to a patient in an amount ranging from 2-3 mg/kg of body weight for at least three days, or at least seven days. In exemplary embodiments, the intravenous administration can be via drip bag infusion or slow IV infusion for a time ranging from 2 to 5 minutes.

In exemplary embodiments, the pharmaceutical compositions disclosed herein can be stored in a syringe possessing a filter with an average pore size of 0.05 μm, 0.10 μm, 0.22 μm, 0.45 μm, 0.70 μm, 0.80 μm, 1 μm, 3 μm, 5 μm, or 10 μm.

EXAMPLES

The present disclosure will be described in more detail with reference to the following Examples, which show exemplary embodiments in accordance with the present disclosure. The present disclosure is not limited to these exemplary embodiments.

The artesunate powders used in the Examples were micronized, packaged into a 60 g Tyvek bags and sterilized with ethylene oxide. The powders were then subjected to the various experimental conditions/tests discussed below.

Example 1: Determining the Effect of Relative Humidity on Powder Bulk Density—Graduated Cylinder In this example, aliquots containing approximately 1-2 g of artesunate powder were subjected to varying relative humidities (20%, 35%, and 50% RH) for approximately 24 hours. The artesunate powders were then passed through a No. 18, 1.00 mm sieve and then added to a 10 mL Cole Parmer graduated cylinder. The volume of each powder was recorded, and the bulk density was calculated. Two replicate measurements were taken, and an average value was calculated. The average bulk densities of the powders are provided in Table 1.

TABLE 1

Bulk Densities of Powder Samples-Graduate Cylinder

| Sample No. | Relative Humidity Exposure | Bulk Density 1 (g/mL) | Bulk Density 2 (g/mL) | Bulk Density 3 (g/mL) | Average Bulk Density (g/mL) |
|---|---|---|---|---|---|
| 1 | 20% | 0.193 | 0.231 | 0.186 | 0.203 |
| 2 | 35% | 0.192 | 0.195 | 0.190 | 0.192 |
| 3 | 50% | 0.200 | 0.208 | 0.201 | 0.203 |

Example 2: Determining the Effect of Relative Humidity on Powder Caking

Scott volumeter (caking) analyses were performed based on USP <616> and under controlled relative humidity conditions on artesunate powders. Artesunate powder samples were poured into a funnel with a 1.0 mm sieve and allowed to fall through 4 glass baffles into a cylinder cup below (25.00±0.05 mL volume with an inside diameter of 30.00±2.00 mm). A pre-weight of the empty cylinder cup was taken prior to experiment. After the cup was full, a spatula was used to level and remove excess powder from the cup. Material was also removed from the sides of the cup, if present. A weight of the full cup was taken to calculate the bulk density, in g/mL, by using the following formula: Bulk density=$M/V_0$; triplicate tests were attempted for each sample. The results of this example are presented in Table 2.

TABLE 2

Bulk Densities of Powder Samples-Scott Volumeter

| Sample No. | $V_0$ (mL) | Relative Humidity Exposure | Bulk Density 1 (g/mL) | Bulk Density 2 (g/mL) | Bulk Density 3 (g/mL) | Average Bulk Density (g/mL) |
|---|---|---|---|---|---|---|
| 1 | 25 | 20% | * | * | * | * |
| 2 | 25 | 35% | 0.178 | 0.180 | * | 0.179 |
| 3 | 25 | 50% | 0.170 | 0.187 | 0.192 | 0.183 |
| 4 | 25 | 60% | 0.161 | 0.160 | * | 0.161 |

* represents parameters that could not be determined during the experiment due to significant powder loss during filling of the cup. The significant powder loss can be attributed to high static cling of the powders to the funnel, the sieve and/or the glass baffles.

Example 3: Determining the Effect of Relative Humidity on Powder Tapped Density In this example, aliquots containing approximately 1-2 g of artesunate powder were subjected to varying relative humidities (20%, 35%, and 50% RH) for approximately 24 hours. The artesunate powders were then passed through a No. 18, 1.00 mm sieve and then added to a 10 mL Cole Parmer graduated cylinder. The graduated cylinder containing the artesunate powders was placed on a Caleva tapped density tester. The samples in the graduated cylinder were then subjected to the following sequence: 10 taps, 500 additional taps, 1250 additional taps, and 1250 additional taps. A volume was taken at the end of each set of taps, and when the volume was consistent for two sets in a row, the measurement was terminated. This final volume was then used to calculate the tapped density. Two replicate measurements were taken, and an average value was calculated. The results of this example are provided in Table 3.

TABLE 3

Tapped Densities of Powder Samples

| Sample No. | Relative Humidity Exposure | Bulk Density 1 (g/mL) | Bulk Density 2 (g/mL) | Bulk Density 3 (g/mL) | Average Bulk Density (g/mL) |
|---|---|---|---|---|---|
| 1 | 20% | 0.307 | 0.318 | 0.283 | 0.303 |
| 2 | 35% | 0.317 | 0.300 | 0.337 | 0.318 |
| 3 | 50% | 0.320 | 0.312 | 0.319 | 0.317 |

Example 4: Determining the Effect of Relative Humidity on Powder Angle of Repose Angle of repose analyses were performed on artesunate powders based upon USP <1174> and under controlled relative humidity conditions. Polytetrafluoroethylene (PTFE) funnels with 8, 10 and 12 mm openings (i.e., Funnel 1, Funnel 2 and Funnel 3, respectively) were used in conjunction with a stainless steel receiving cylinder (Ø=30 mm). Powder samples were placed in the funnel while the funnel opening was closed with a glass slide. Once all the sample powder was loaded in the funnel, the glass slide was removed to allow powder to land on the cylinder below. The top and side of the funnel were tapped to enable the sample powder to drop down. The funnel height was maintained approximately 2-4 cm from the top of the powder pile to minimize the impact of falling powder on the tip of the cone. After the powder cone was built, height of the material forming the cone (h) and the radius (r) of the base were measured by a metal ruler. The angle of repose ($\theta$) was calculated as follows: $\tan(\theta) = h/r$. Results were only considered valid when a symmetrical cone of powder was formed. Triplicate tests were attempted for each size of the funnels with the same amount of material being used. The results of this example are presented in Tables 4 and 5.

TABLE 4

Angle of Repose of Powder Samples at 50% RH

|  | height 1 (mm) | height 2 (mm) | height 3 (mm) | average height (mm) | angle of repose (degrees) |
|---|---|---|---|---|---|
| Funnel 1 | 12 | 15 | 13 | 13 | 42 |
| Funnel 2 | 16 | 14 | 15 | 15 | 45 |
| Funnel 3 | 15 | 13 | 13 | 14 | 42 |
| Average |  |  |  |  | 43 |

TABLE 5

Angle of Repose of Powder Samples at 35% RH

|  | height 1 (mm) | height 2 (mm) | height 3 (mm) | average height (mm) | angle of repose (degrees) |
|---|---|---|---|---|---|
| Funnel 1 | 10 | 10 | 11 | 10 | 35 |
| Funnel 2 | 12 | 12 | 11 | 12 | 38 |
| Funnel 3 | 16 | 15 | 14 | 15 | 45 |
| Average |  |  |  |  | 39 |

The above characterization data demonstrates that the artesunate powder exhibited a reduced flowability based on the angle of repose at 50% relative humidity. Based on USP 1174, angle of repose at 50% relative humidity indicated the flow property was passable but may hang up. The flow properties at 35% relative humidity were acceptable based on USP 1174 and aid was not needed.

Figure 1:
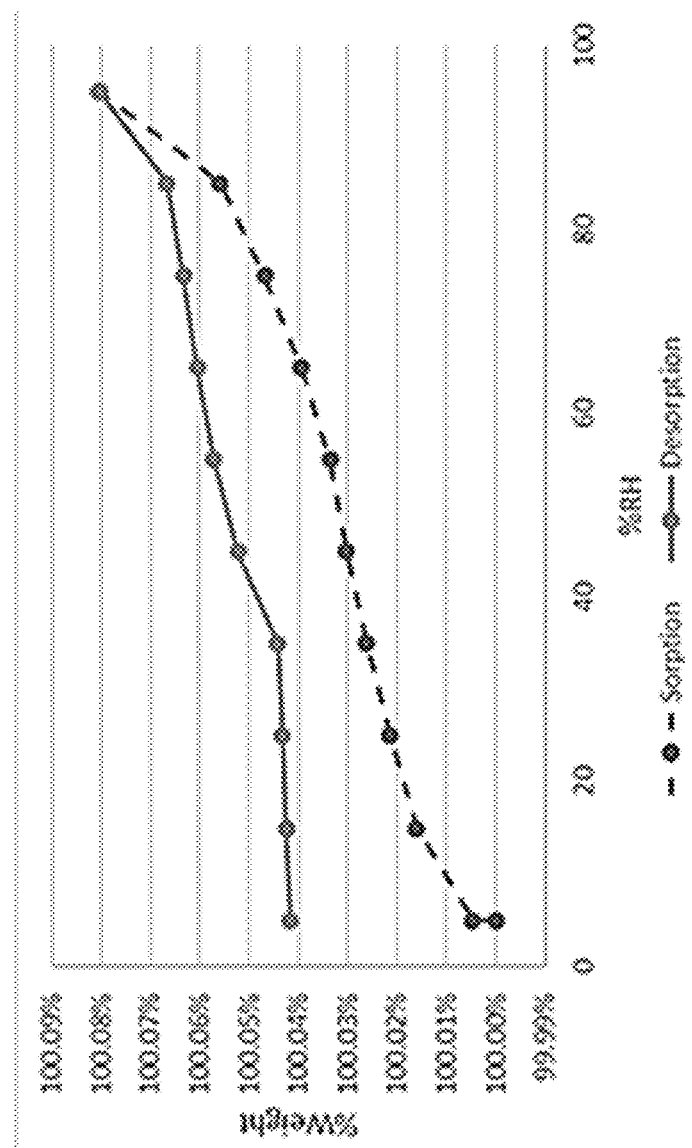
FIG. 1 depicts the results of a DVS analysis for an exemplary artesunate powder sample that was equilibrated to 20% RH. The graph depicts the artesunate powder's moisture sorption and desorption at varying RH levels.
Figure 2:
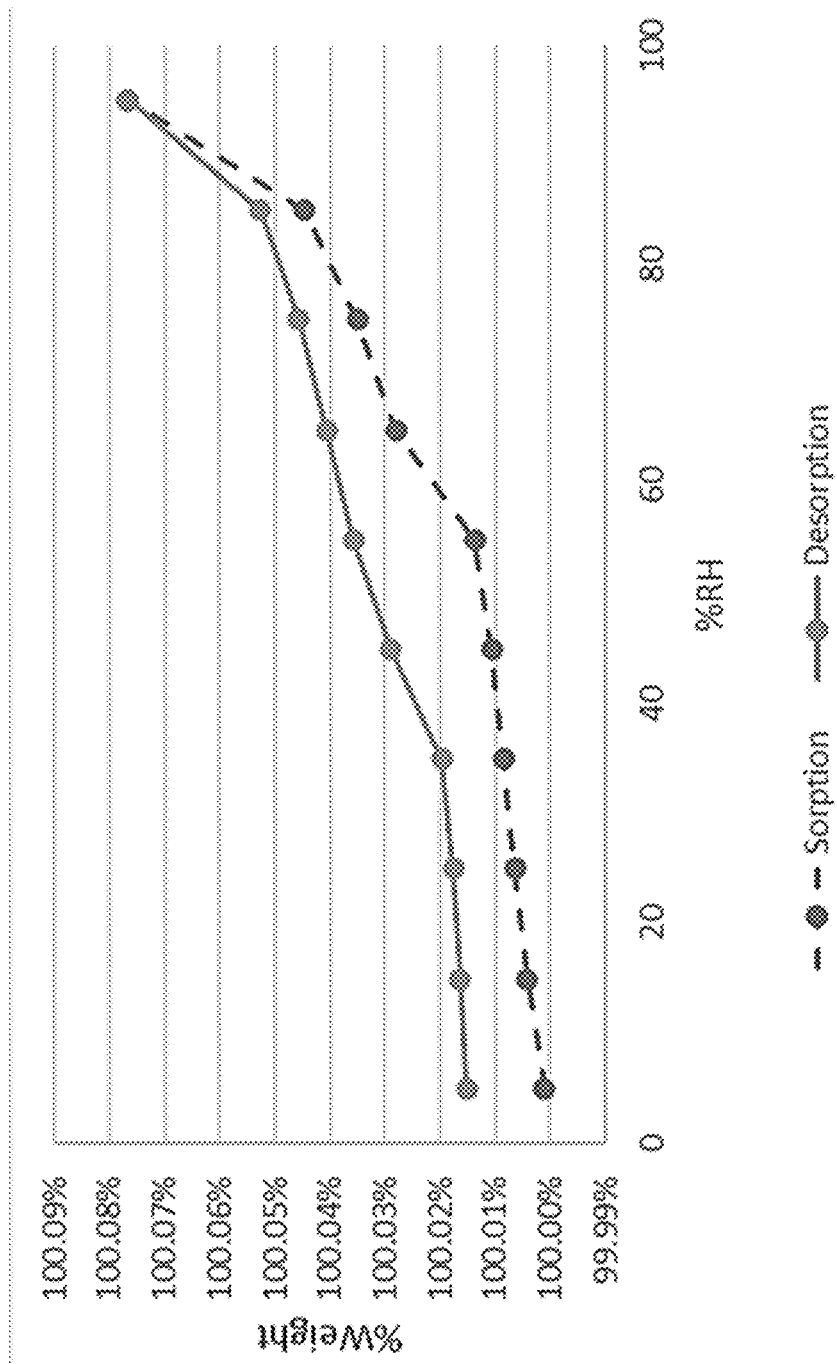
FIG. 2 depicts the results of a DVS analysis for an exemplary artesunate powder sample that was equilibrated to 50% RH. The graph depicts the artesunate powder's moisture sorption and desorption at varying RH levels.

Example 5: Determining the Effect of Relative Humidity on Powder Moisture Absorbance DVS analyses were carried out on artesunate powder samples using two TA Instruments Q5000 Dynamic Vapor Sorption analyzers. The instruments were calibrated with standard weights and a sodium bromide standard for humidity. One sample was equilibrated 50% RH for at least 5 days prior to analysis, while the other sample was equilibrated to 20% RH for at least 5 days prior to analysis. Approximately 10 to 20 mg of the powder samples were loaded into metal-coated quartz pans for analysis. The samples were analyzed at 25° C. in 10% RH steps from 5 to 95% RH (adsorption cycle) and from 95 to 5% RH (desorption cycle). The movement from one step to the next occurred either after satisfying the equilibrium criterion of 0.01% weight change in 30 minutes or, if the equilibrium criterion was not met, after 90 minutes. The percent weight change values were calculated using Microsoft Excel® 2016. The results of this example are provided in Tables 6 and 7 and depicted in FIG. 1 (Sample Equilibrated to 20% RH) and FIG. 2 (Sample Equilibrated to 50% RH).

TABLE 6

DVS Results of Sample Equilibrated to 20% RH

| RH step | Mass of Powder Sample (g) | Time (Total Min) | % change | Time (Step Hrs) |
|---|---|---|---|---|
| 5 | 16.59231 | 0 | 100.00% | 0 |
| 5 | 16.59308 | 60 | 100.00% | 1 |
| 15 | 16.59497 | 90 | 100.02% | 0.5 |
| 25 | 16.59587 | 120 | 100.02% | 0.5 |
| 35 | 16.59666 | 150 | 100.03% | 0.5 |
| 45 | 16.59735 | 180 | 100.03% | 0.5 |
| 55 | 16.59788 | 210 | 100.03% | 0.5 |
| 65 | 16.59886 | 240 | 100.04% | 0.5 |
| 75 | 16.60009 | 270 | 100.05% | 0.5 |
| 85 | 16.60158 | 300 | 100.06% | 0.5 |
| 95 | 16.60567 | 360 | 100.08% | 1 |
| 85 | 16.60338 | 390 | 100.07% | 0.5 |
| 75 | 16.60283 | 420 | 100.06% | 0.5 |
| 65 | 16.60234 | 450 | 100.06% | 0.5 |
| 55 | 16.60179 | 480 | 100.06% | 0.5 |
| 45 | 16.60098 | 510 | 100.05% | 0.5 |
| 35 | 16.59966 | 540 | 100.04% | 0.5 |
| 25 | 16.59948 | 570 | 100.04% | 0.5 |
| 15 | 16.59936 | 600 | 100.04% | 0.5 |
| 5 | 16.59924 | 630 | 100.04% | 0.5 |

TABLE 7

DVS Results of Sample Equilibrated to 50% RH

| RH step | Mass of Powder Sample (g) | Time (Total Min) | % change | Time (Step Hrs) |
|---|---|---|---|---|
| 5 | 16.79424 | 0 | 100.00% | 0 |
| 5 | 16.7942 | 30 | 100.01% | 0.5 |
| 15 | 16.79472 | 60 | 100.01% | 0.5 |
| 25 | 16.79508 | 90 | 100.01% | 0.5 |
| 35 | 16.79545 | 120 | 100.01% | 0.5 |
| 45 | 16.79579 | 150 | 100.02% | 0.5 |
| 55 | 16.79632 | 180 | 100.02% | 0.5 |
| 65 | 16.79873 | 240 | 100.03% | 1 |
| 75 | 16.79988 | 270 | 100.04% | 0.5 |
| 85 | 16.8015 | 300 | 100.05% | 0.5 |
| 95 | 16.8069 | 360 | 100.08% | 1 |
| 85 | 16.80286 | 420 | 100.06% | 1 |
| 75 | 16.80168 | 450 | 100.05% | 0.5 |
| 65 | 16.80083 | 480 | 100.05% | 0.5 |
| 55 | 16.8 | 510 | 100.04% | 0.5 |
| 45 | 16.79888 | 540 | 100.03% | 0.5 |
| 35 | 16.79733 | 570 | 100.02% | 0.5 |
| 25 | 16.79696 | 600 | 100.02% | 0.5 |
| 15 | 16.79676 | 630 | 100.02% | 0.5 |
| 5 | 16.79656 | 660 | 100.02% | 0.5 |

Example 6: Determining the Effect of Relative Humidity on Powder Static Charge Samples of artesunate powder were placed under controlled relative humidity conditions (approximately 10%, 20%, 30%, 40%, and 50%) for at least five days. Static charge measurements were performed using a Newtry static meter. The powders were accumulated onto a piece of weigh paper and the surface gently leveled. The static meter was held approximately 25 millimeters from the surface of the material to obtain a reading. Three replicate measurements were taken, and an average was calculated. Results from this example are provided in Table 8.

TABLE 8

Static Charges of Powder Samples

| Sample No. | Relative Humidity Exposure | Static Reading 1 (kV) | Static Reading 2 (kV) | Static Reading 3 (kV) | Average Static Reading (kV) |
|---|---|---|---|---|---|
| 1 | 10% | 0.40 | 0.38 | 0.30 | 0.36 |
| 2 | 20% | 0.12 | 0.13 | 0.13 | 0.13 |
| 3 | 30% | −0.04 | −0.04 | −0.04 | −0.04 |
| 4 | 40% | 0.02 | 0.01 | 0.00 | 0.01 |
| 5 | 50% | −0.05 | −0.05 | −0.05 | −0.05 |

The artesunate powders demonstrated a significant static charge that varied at different relative humidity levels. The average static reading at 1% RH was 0.36 kV and 22% RH was 0.13 kV while the average static reading at 30% RH, 40% RH, and 50% RH were −0.04 kV, 0.01 kV, and −0.05 kV respectively.

Example 7: Determining the Variable Humidity X-Ray Powder Diffraction of the Powders Variable Humidity X-ray Powder Diffraction (VH-XRPD) experiments were carried out on artesunate powder samples at 25° C. using four preprogrammed humidity steps, each one hour in duration. Three XRPD scans, each 18 minutes long, were performed during each step. Scan parameters are shown in Table 9.

TABLE 9

Scan Parameters for VH-XRPD

| | | | | | |
|---|---|---|---|---|---|
| Operator: | bmibeck | Date: | Jan. 5, 2024 | Sample: | |
| Spin Rate(RPM): | None | Memo: | | File Name: | |
| Mode: | CONTINUOUS | Axis: | TwoThetaTheta | User Speed(°/min): | NA |
| Speed(°/min): | 2.0000 | Start(°2θ): | 3.0000 | End(°2θ): | 40.0000 |
| Step(°2θ): | 0.0100 | mA: | 50 | kV: | 40 |
| Slit 0: | 1/3deg | Slit 1: | 8.000 mm | Slit 2: | 13.100 mm |
| CBO: | BB_CB | Filter: | Cu_K-beta_1D | X-ray Tube: | Cu |

The humidity and temperature of each powder sample was monitored and recorded every second during the experiment. Table 10 compares the setpoint to the average and variance of these recorded values.

TABLE 10

Comparison of Programed Setpoints and Measured Process Variables

| | Temperature, ° C. | | | Humidity, % RH | | |
|---|---|---|---|---|---|---|
| Step | Set-point | Average | Variance | Set-point | Average | Variance |
| 0 | na | 23.9 | 0.2 | na | 18.2 | 0.5 |
| 1 | 25 | 25 | 0 | 20 | 20.0 | 0.1 |
| 2 | 25 | 25 | 0 | 40 | 30.4 | 1.8 |
| 3 | 25 | 25 | 0 | 50 | 40.0 | 0.1 |
| 4 | 25 | 25 | 0 | 20 | 20.0 | 0.1 |

Figure 3:
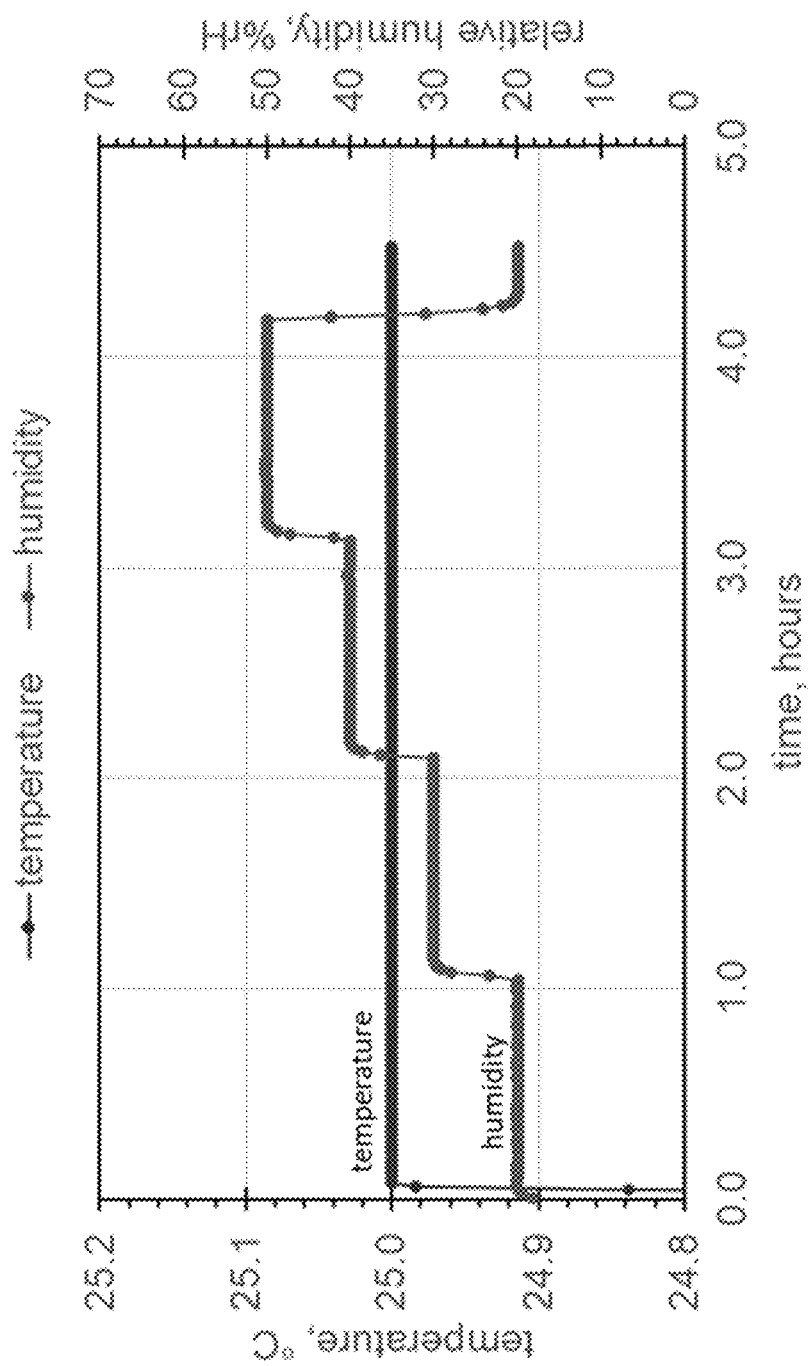
FIG. 3 is a measured temperature versus relative humidity plot that depicts the results from a VH-XRPD experiment performed on an exemplary artesunate powder.

FIG. 3 shows the measured temperature versus relative humidity plot in the VH-XRPD experiment.

A Rigaku SmartLab X-Ray Diffractometer was combined with an Anton Paar Combined Cryo Humidity CHC plus+ (CHC+) chamber. The CHC+ system consists of a chamber with both temperature and humidity control. The X-ray Diffractometer was operated in Bragg-Brentano reflection geometry equipped with a beam stop and knife edge to reduce incident beam and air scatter. The scan range is from 2θ angle of 3° to 40°.

A humidity controller operated with distilled water and house compressed air used closed-loop feedback from a precision humidity sensor to maintain a preprogrammed humidity setpoint. Additionally, the chamber wall temperature was controlled with a circulator bath to prevent the formation of a humidity gradient. The humidity in the space above the sample was controlled using the combination of temperature measured at the sample and the temperature and humidity measured at the wall.

Example 8: Determining the X-Ray Powder Diffraction Peaks of the Powders

Artesunate powder samples for XRPD analysis were placed in a 10 mm×0.2 mm well of a zero-background Si sample holder. The sample material was distributed evenly in the well and leveled with the reference surface (top) using a frosted glass slide.

A Rigaku SmartLab X-Ray Diffractometer was configured in Bragg-Brentano reflection geometry equipped with a beam stop and knife edge to reduce incident beam and air scatter. Data collection parameters are shown in Table 11.

Figure 4:
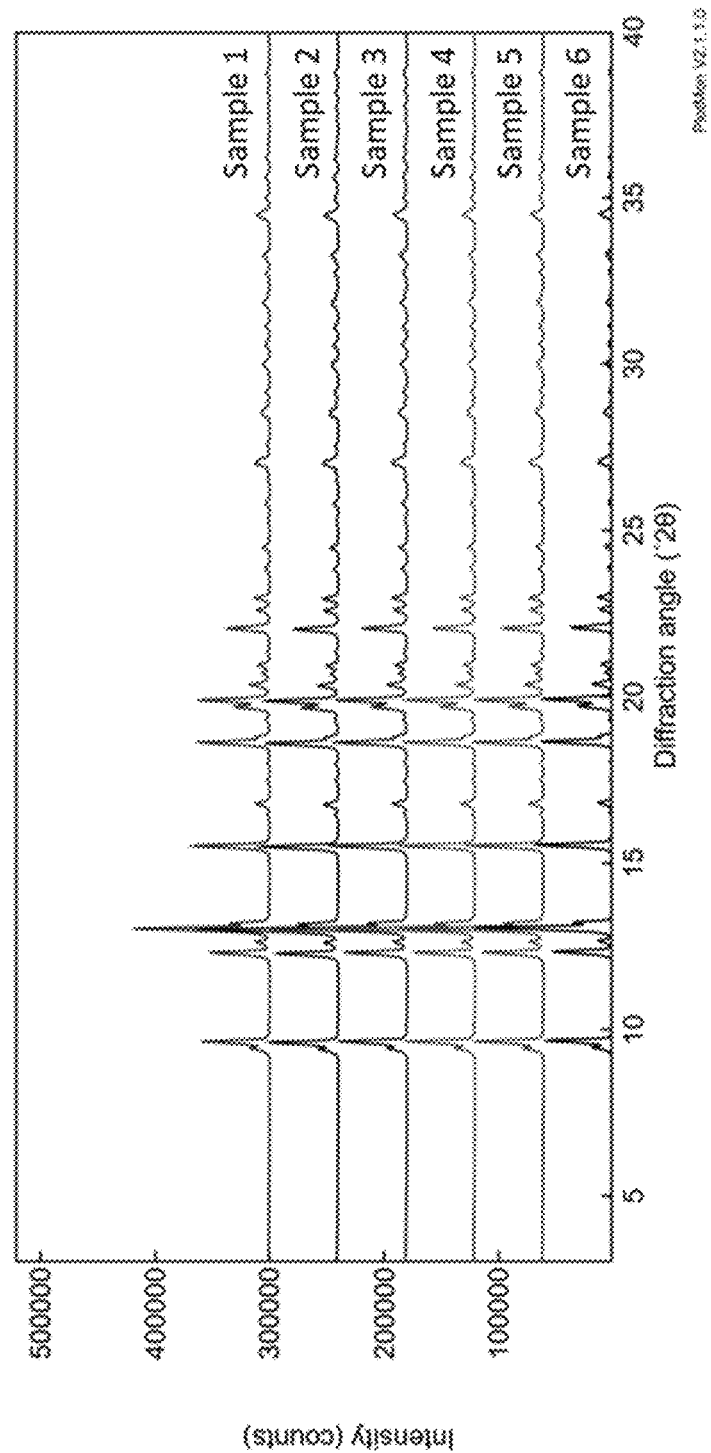
FIG. 4 is an XRPD analysis plot that depicts the diffraction angles for six exemplary artesunate powders.
Figure 5:
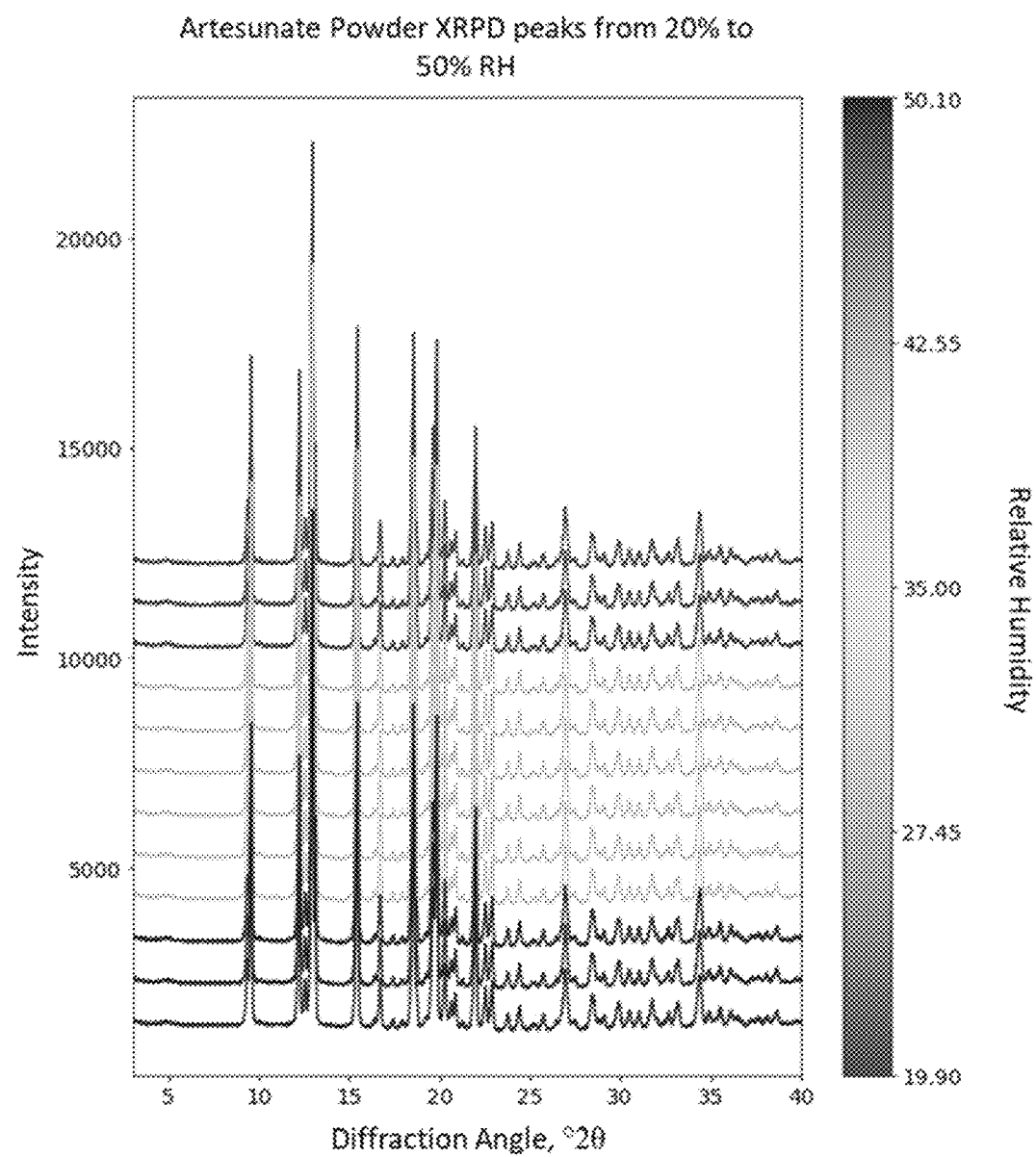
FIG. 5 is a waterfall plot that depicts the diffraction angles for an exemplary artesunate powder under varying relative humidity levels.

TABLE 11

XRPD Data Collection Parameters

| Parameter | Value | Parameter | Value |
|---|---|---|---|
| Geometry | Bragg-Brentano | Receiving Slit 1 (mm) | 18 |
| Tube Anode | Cu Kα | Receiving Slit 2 (mm) | 20.1 |
| Tube Type | Long Fine Focus | Start Angle 2θ (°) | 2 |
| Tube Voltage (kV) | 40 | End Angle 2θ (°) | 40 |
| Tube Current (mA) | 44 | Step Size (°) | 0.02 |
| Detector | HyPix-3000 | Scan Speed (°/min) | 6 |
| Monochromatization | Kβ Filter | Spinning (rpm) | 11 |
| Incident Slit (°) | 1/3 | Sample Holder | Silicon low background holder |

FIGS. 4 and 5 display the results of the XRPD experiments.

Example 9: Gathering Scanning Electron Microscopy Data

SEM images were collected using a Phenom XL Desktop SEM equipped with a $CeB_6$ electron source (see FIG. 6). Phenom User Interface version 1.4 was used to acquire and save the images. Detailed image parameters are recorded in the footer of each image.

Powder sample preparation for proper SEM results is known to those skilled in the art, and mainly relies on a proper monolayer of particles. These can be prepared with: the flick method, wherein a cotton swab is used to disperse particles onto a sample support by the "flick of a finger"; drop casting, where liquid solvents transfer particles onto a sample stub; or the dish method, where particles are spread over the area of a petri dish or similar flat surface using a spatula. A Nebula Particle Dispenser may also be used to prepare a uniform layer of powder. Although it is desirable to avoid agglomeration, the example as described herein sought to determine when agglomeration occurs at particular humidity levels. The samples tested herein were prepared with the flick method.

FIG. 6 display the results of micronized artesunate powder at 20% RH. All of FIGS. 6A-6D show a strong caking, or agglomeration, at 20% RH. Moderate agglomeration is reflected in the large clumps of powder material which do not show significant separation from the remaining material at any magnification.

FIG. 7 displays the results of micronized artesunate powder at 35% RH. The images show less caking as reflected by the smaller masses in the photographs at each magnification.

FIG. 8 displays the results of micronized artesunate powder at 50% RH, where significant agglomeration, or caking, is observed. All images showing at different magnifications show a significant level of caking above and beyond the 35% RH levels.

Without being bound to any particular theory, exposure of the micronized artesunate powder at 35% RH is believed to improve the flowability and the filling accuracy of the micronized powder by reducing the overall aggregation and agglomeration of the powder, thereby allowing it to more freely traverse through a dosing head without clogging.

Each SEM photograph also shows with particularity the altered shape of the artesunate powder after micronization. Artesunate powder, without micronization, typically possess a "plate" shape with two flat surfaces. After micronization, a more rounded, spherical version of the powder can be observed. This rounder, more spherical shape of the powder can aid in the dispensing of the powder from a dosing head since it does not engage with the dosing head surface as frequently as the plate shape of non-micronized artesunate powders.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

What is claimed is:

1. A micronized powder comprising:
a therapeutically effective amount of 4-oxo-4-[[(1R,4S,5R,8S,9R,10S,12R,13R)-1,5,9-trimethyl-11,14,15,16-tetraoxatetracyclo[10.3.1.0$^{4,13}$.0$^{8,13}$]hexadecan-10-yl]oxy]butanoic acid (artesunate) or a pharmaceutically acceptable salt thereof,
wherein the micronized powder contains:
(i) a crystalline form of artesunate or the pharmaceutically acceptable salt thereof in a concentration above 0 wt % to about 1 wt % of the total weight of the powder, and
(ii) has an average static charge from −0.05 kV to 0.05 kV according to a static charge test that includes: (i) subjecting the powder to a relative humidity of 30% to 40% for at least five days, (ii) placing the powder onto a piece of weighing paper, (iii) measuring the static charge of the powder with a static meter at least three times, wherein the measuring of the static charge of the powder with a static meter occurs at least 25 millimeters from the surface of the powder, and (iv) calculating the average static charge from the measured static charges,
wherein the micronized powder has been prepared according to a process comprising:
(i) packaging the micronized powder into at least three polyethylene fiber containers,
(ii) sterilizing the micronized powder with ethylene oxide while packaged in the at least three polyethylene fiber containers, and
(iii) filling the sterilized micronized powder into a container at a relative humidity of 30% to 40% at a temperature from 15° C. to 30° C.

2. The powder of claim 1, wherein the powder absorbs moisture in an amount from 0.01 wt % to 0.03 wt %, based on the total weight of the powder, when subjected to a relative humidity from 30% to 40%.

3. The powder of claim 2, wherein the powder has an angle of repose of less than 40° when passing through a funnel with an opening of 8 mm to 12 mm at a relative humidity from 30% to 40%.

4. The powder of claim 3, wherein the powder is micronized to a particle size possessing a D90 of less than 20 μm, a D100 of less than 100 μm, or a D50 of less than 5 μm.

5. The powder of claim 4, wherein the artesunate or pharmaceutically acceptable salt thereof is free of *Corynebacterium auris* growth.

6. The powder of claim 5, wherein the powder comprises no more than 0.5% water, no more 0.5% dihydroartemisinin, no more 0.2% didehydrodeoxyartemisinin, and no more 0.2% of other impurities.

7. The powder of claim 6, wherein the powder has a Hausner ratio of at least 1.6 when subjected to a relative humidity from 30% to 40%.

8. The powder of claim 7, wherein the crystalline form of artesunate or the pharmaceutically acceptable salt thereof is 10-α artesunate.

9. The powder of claim 8, wherein the powder has a bulk density below 0.2 g/mL when subjected to a relative humidity from 30% to 40%.

10. The powder of claim 9, wherein the powder has a tap density above 0.3 g/mL when subjected to a relative humidity from 30% to 40%.

11. The micronized powder according to claim 1, further comprising a buffer solution.

12. The pharmaceutical composition of claim 11, wherein the buffer solution is a phosphate buffer solution.

13. The pharmaceutical composition of claim 12, wherein the phosphate buffer solution includes sodium phosphate monobasic monohydrate, sodium phosphate dibasic dihydrate, sodium hydroxide, phosphoric acid and water.

14. A process for the preparation of the powder as defined in claim 1, the process comprising:
micronizing a raw artesunate ingredient into an artesunate powder,
packaging the micronized powder Into at least three polyethylene fiber containers,
sterilizing the micronized powder with ethylene oxide while packaged in the at least three polyethylene fiber containers, and
filling the sterilized micronized powder Into a container at a relative humidity of 30% to 40% at a temperature of from 15° C. to 30° C.

15. The process of claim 14, wherein the filing the sterilized artesunate powder occurs under aseptic conditions.

16. The process of claim 14, wherein the filling of the sterilized artesunate powder is performed with a dosing system equipped with a dosing head having an opening of at least 2.5 mm.

17. The process of claim 16, wherein the sterilized artesunate powder is pre-mixed in the dosing head of the dosing system before being filled into a container.

18. The process of claim 17, wherein the container is a depyrogenated borosilicate clear glass vial.

* * * * *